United States Patent [19]

Srinivasan

[11] Patent Number: 5,798,830
[45] Date of Patent: Aug. 25, 1998

[54] METHOD OF ESTABLISHING THRESHOLDS FOR IMAGE COMPARISON

[75] Inventor: Lakshman Srinivasan, San Jose, Calif.

[73] Assignee: Ultrapointe Corporation, San Jose, Calif.

[21] Appl. No.: 757,491

[22] Filed: Nov. 27, 1996

Related U.S. Application Data

[63] Continuation-in-part of Ser. No. 497,162, Jun. 30, 1995, abandoned, which is a continuation-in-part of Ser. No. 80,014, Jun. 17, 1993, Pat. No. 5,479,252.

[51] Int. Cl.$^6$ ........................................... G01N 21/00
[52] U.S. Cl. ................... 356/237; 356/369; 250/559.42; 250/559.48
[58] Field of Search ........................ 356/237, 369, 356/375; 250/559.42, 559.48

[56] References Cited

U.S. PATENT DOCUMENTS 2,758,502  8/1956  Scott et al. ........................ 88/14
5,479,252  12/1995  Worster ........................... 356/237

*Primary Examiner*—Frank G. Font
*Assistant Examiner*—Reginald A. Ratliff
*Attorney, Agent, or Firm*—Skjerven, Morrill, MacPherson, Franklin & Friel LLP; Alan H. MacPherson

[57] ABSTRACT

A method is described for optimizing intensity-comparison thresholds used to compare test and reference images for defect detection. Intensity differences between corresponding pixels in the two images that exceed a predefined threshold value are deemed defect pixels. According to the method, the pixels of the reference image are grouped according to their respective z values (elevation) to identify different physical layers of the reference surface. Because different surface layers can have different image properties, such as reflectance and image texture, the groups of pixels are analyzed separately to determine an optimal threshold value for each of the groups, and therefore for each layer of the reference surface.

20 Claims, 4 Drawing Sheets

METHOD OF ESTABLISHING THRESHOLDS FOR IMAGE COMPARISON

CROSS-REFERENCES TO RELATED APPLICATIONS

The present application is a continuation-in-part of commonly owned application Ser. No. 08/497,162 now abandoned, filed on 30 Jun. 1995, abandoned, entitled "Method for Characterizing Defects on Semiconductor Wafers," by Bruce W. Worster and Ken K. Lee, which is a continuation-in-part of commonly owned application Ser. No. 08/080,014 now U.S. Pat. No. 5,479,252, filed on 17 Jun. 1993, entitled "Laser Imaging System For Inspection and Analysis of Sub-Micron Particles," by Bruce W. Worster, Dale E. Crane, Hans J. Hansen, Christopher R. Fairley, and Ken K. Lee. The present application is related to the following commonly owned, co-pending U.S. patent applications:

1. "A Method and Apparatus for Performing an Automatic Focus Operation," by Timothy V. Thompson, Christopher R. Fairley, and Ken K. Lee, application Ser. No. 08/183,536 now U.S. Pat. No. 5,843,055, filed on 18 Jan. 1994;
2. "A Method and Apparatus for Automatic Focusing of a Confocal Laser Microscope," by Christopher R. Fairley, Timothy V. Thompson, and Ken K. Lee, application Ser. No. 08/373,145, filed on 17 Jan. 1995;
3. "Surface Extraction from a Three-Dimensional Data Set," by Ken K. Lee, application Ser. No. 08/079,193, filed on 17 Jun. 1993, now Statutory Invention Registration No. H1530;
4. "Surface Data Processor," by Abigail A. Moorhouse, Christopher R. Fairley, Phillip R. Rigg, and Alan Helgesson, application Ser. No. 08/198,751 now U.S. Pat. No. 5,557,113, filed on 18 Feb. 1994;
5. "Automated Surface Acquisition For a Confocal Microscope," by Ken Kinsun Lee, application Ser. No. 08/483,234 now U.S. Pat. No. 5,594,235, filed on 7 Jun. 1995;
6. "Method for Forecasting the Effects of Defects on Semiconductor Wafers," by Ken K. Lee, Bruce W. Worster, and John M. Scott, application Ser. No. 08/730,283 still pending, filed on 30 Jun. 1995; and
7. "Method for Characterizing Defects on Semiconductor Wafers," by Ken K. Lee, et al., application Ser. No. 08/576,420 still pending, filed herewith.

These applications are incorporated herein by this reference.

BACKGROUND

Defects, such as structural flaws, process residues, and external contamination, occur during the production of semiconductor wafers. Defects are typically detected by a class of instruments called defect scanners. Such instruments automatically scan wafer surfaces and detect optical anomalies using a variety of techniques. The locations of these anomalies with respect to the pattern of semiconductor devices on the wafer surface are recorded. This information, or "defect map," is stored in a computer file and sent to a defect review station.

Using the defect map to locate each defect, a human operator observes each defect under a microscope and classifies each defect according to type (e.g., particle, pit, scratch, or contaminant). Information gained from this process is used to correct the source of defects, and thereby improve the efficiency and yield of the semiconductor production process. Unfortunately, people are relatively slow and are quickly fatigued by the highly repetitive task of observing and classifying defects.

Methods of automatically classifying defects, collectively known as Automatic Defect Classification, or "ADC," have been developed to overcome the disadvantages of manual defect classification. (ADC alternatively stands for Automatic Defect Characterization.) In conventional ADC, review stations are automated to load a wafer that has been mapped for defect location by a defect scanner. The defect area is then imaged and compared to a reference image. The reference image may be a previously stored data-base image of a corresponding known-good area of the same or a similar die on the same or on a similar wafer, or it may be a specific image taken from, e.g., an adjacent die. The reference image is compared with the image containing the defect. Differences measured between the two images indicate the location and extent of the defect.

Conventional ADC systems work well to detect, characterize, and classify defects. However, if the comparison of test and reference images is too sensitive, many test surfaces are incorrectly deemed defective due to normal differences between test and reference surfaces and due to different image characteristics resulting from, for example, the test and reference images being imaged at different focal points or intensities. For this reason, corresponding pixels are compared using an intensity-error threshold: if the difference between the image intensities of corresponding test and reference pixels does not exceed the error threshold, then the difference is not deemed the result of a defect.

The use of an error threshold decreases the instances of false defect detection. Unfortunately, it also decreases the sensitivity with which defects are detected. Accordingly, great care is taken to optimize the error threshold for a given image comparison. Still, there remains a demand for error-threshold optimization methods that further improve defect detection.

SUMMARY

The present invention is directed, in part, to an improved error-threshold optimization method. According to the method, a reference surface is imaged in three dimensions and described as an array of pixels each having a unique x-y coordinate, a z coordinate, and an intensity value I.

Different physical layers of a given surface are typically of different types of materials, and therefore exhibit different image properties. For example, a particular layer on a semiconductor substrate may be of pure silicon, silicon dioxide, metal, or photoresist. In accordance with an embodiment of the invention, the pixels representing the reference surface are grouped by elevation (i.e., Z) to identify separate physical layers of the reference surface. Each group of pixels is then separately analyzed to establish an optimum intensity error threshold for each physical layer.

BRIEF DESCRIPTION OF THE FIGURES

These and other features, aspects, and advantages of the present invention will become better understood with regard to the following description, appended claims, and accompanying figures, where:

DETAILED DESCRIPTION

Figure 1:
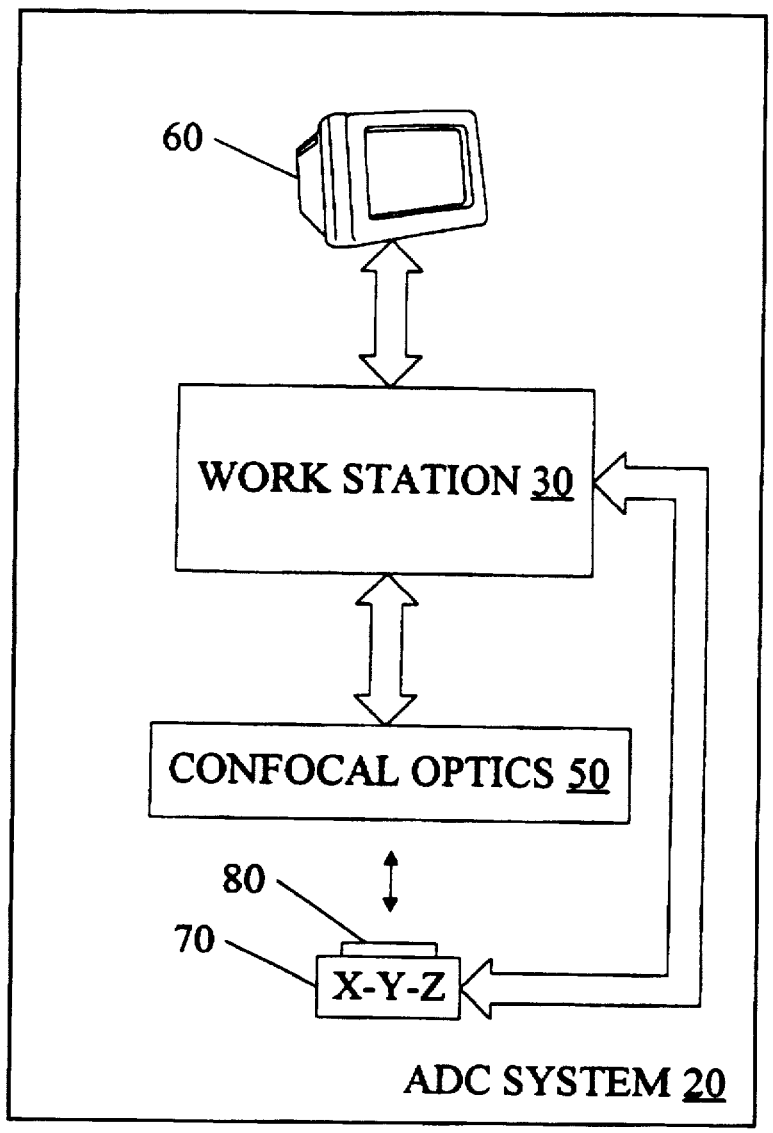
FIG. 1 is a block diagram of a conventional defect scanner 10 connected to an ADC system 20.

FIG. 1 is a block diagram of an ADC system 20. ADC system 20 includes a workstation 30 that supports both a laser imaging system (LIS) and the ADC process. The LIS conventionally includes confocal optics 50, a display 60, and an X-Y-Z translation stage 70, and is configured to image a reference surface. In FIG. 1 that reference surface is a surface of a semiconductor wafer 80. For a more detailed discussion of an LIS for use in the present invention, see the above-incorporated patent entitled "Laser Imaging System For Inspection and Analysis of Sub-Micron Particles."

A three-dimensional image of a surface is obtained using confocal optics 50, preferably of a laser-based confocal microscope. To obtain an image of a surface using confocal optics 50, a beam of light passes through an objective lens and is scanned across the surface from a number of locations along the z axis. The scanned laser beam generates a number of signals at each z location, each of the signals representing an intensity of light reflected through the objective lens from a given point on the surface. The group of signals provided by an x-y scan from a single z location of the objective lens is called a "slice" of intensity data. Slices taken from a number of locations along the z axis overlap to form a three-dimensional set of reflected intensity data, hereafter referred to as a "volumetric data set."

A pair of surface arrays, $S_I$ and $S_Z$, may be derived from a volumetric data set extracted by a confocal microscope by determining, for each x-y coordinate, the maximum intensity value, $I_{max}$, and the Z coordinate corresponding to the maximum intensity value. (For simple reflective surfaces, the confocal response of the LIS is a maximum at the surface.) The surface-intensity array $S_I$ may be represented as:

$S_I$ (X, Y, $I_{max}$), and the array of z coordinates corresponding to the maximum intensity values may be represented as:

$S_Z$ (x, y, $Z_{Imax}$), where $Z_{Imax}$ represents the Z coordinate corresponding to the point of maximum reflected intensity for a given x-y coordinate.

In one embodiment, surface arrays $S_I$ and $S_Z$ are updated as the ADC system scans the test surface from each Z position. Each intensity value of each slice of intensity data is compared to a maximum intensity value corresponding to the same x-y coordinate in the array of maximum intensity values. If the intensity value of the slice is greater than the corresponding maximum intensity value, then the intensity value of the array of maximum intensity values, $S_I$(x, y, $I_{max}$), is updated with a new maximum intensity value for that x-y coordinate and the array of Z values, $S_z$(x, y, $Z_{Imax}$), is updated with the Z location of the new maximum intensity value. Because the point of maximum reflected intensity gives an indication of the location of the surface, the array of Z values $S_Z$ provides an indication of the surface contour. This second method is faster and requires less memory than is required for generating a complete volumetric data set.

The arrays $S_I$ and $S_Z$ collectively represent image pixels in three dimensions. Hereafter, the term "pixel" refers to a single x-y location corresponding to both array $S_I$ and array $S_Z$.

For a more detailed description of a laser imaging system that employs a confocal microscope, see the co-pending application entitled "Laser Imaging System For Inspection and Analysis of Sub-Micron Particles," the content of which is incorporated herein by reference.

Different physical layers of a given surface are typically of different types of materials, and therefore exhibit different image properties. For example, different layers on a semiconductor substrate may be due to layers of pure silicon, silicon dioxide, metals, or photoresist. In addition to differences in image intensity, different materials exhibit differences in image "texture." For example, some materials, such as pure silicon, produce "smooth" images, which have relatively consistent intensity values from pixel to pixel; other materials, such as aluminum, produce "rough" images, which vary in intensity from one pixel to the next.

Recall that defects are conventionally detected by aligning test and reference images and then subtracting the images one from the other. Intensity differences between corresponding test and reference pixels that exceed an intensity-error threshold indicate the presence of a defect. When the pixels being compared are of a smooth portion of an image, the difference in intensity will, in the absence of defects, be relatively small. Thus, the intensity-error threshold should be made small to achieve the appropriate balance between sensitivity and selectivity. On the other hand, corresponding pixels in rough areas of test and reference images have far greater intensity differences in the absence of a defect. Thus, the error threshold should be greater than that for smooth images.

ADC system 20 takes advantage of the different image properties of different layers by separately analyzing the image properties of each layer to establish an optimum intensity-error threshold $I_{TH}$ for each layer. Thus, in step 215 ADC system 20 collects pixels having similar $Z_{Imax}$ values to separate various physical layers of the reference surface. ADC system 20 then uses the intensity data associated with each group of pixels to assign each group (and therefore each layer) an optimum intensity-error threshold $I_{THL}$.

Figure 2A:
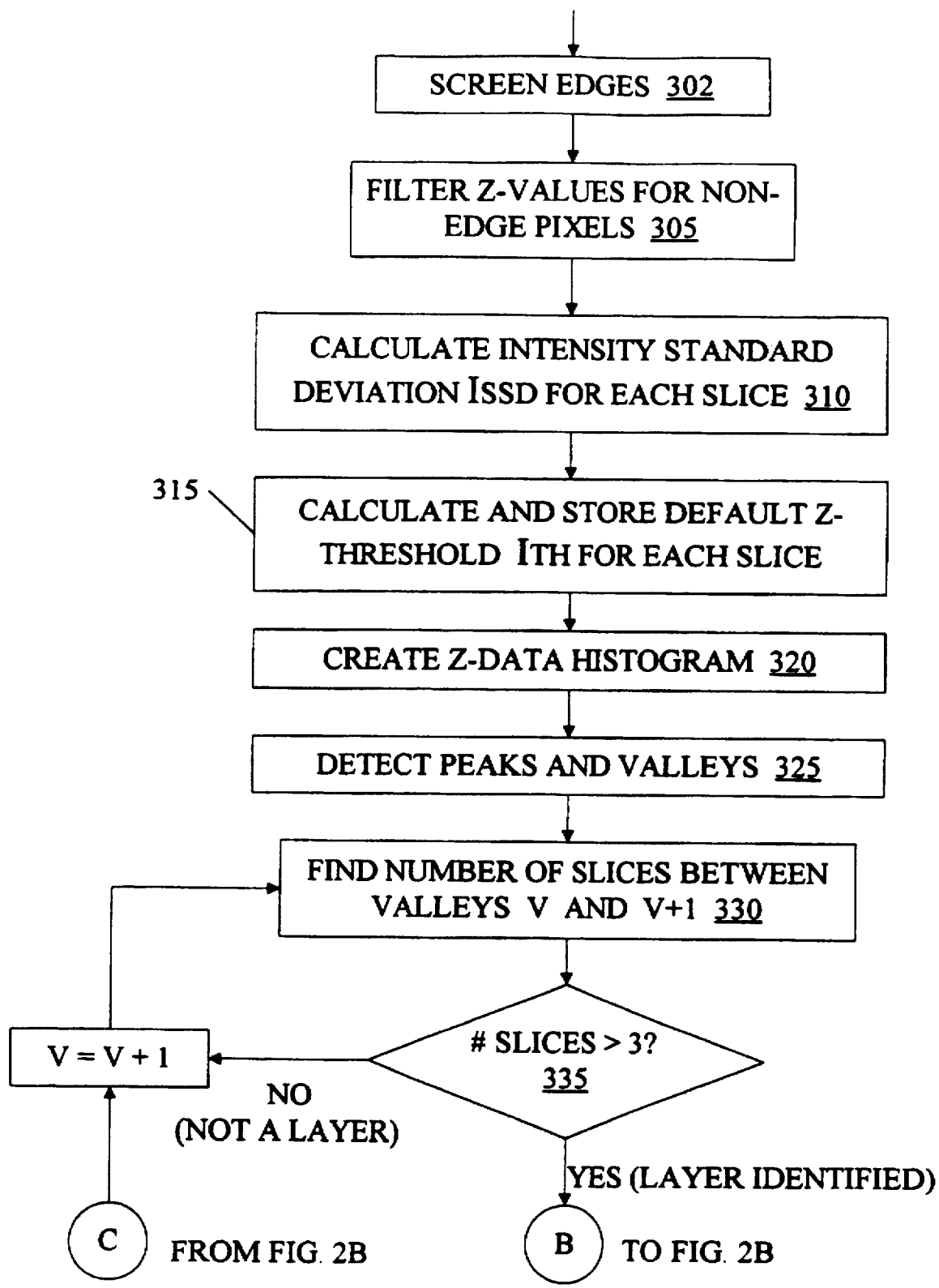
FIGS. 2A and 2B combined are a flowchart depicting the process of establishing multiple error thresholds $I_{TH}$ for a multi-layer reference surface.
Figure 2B:
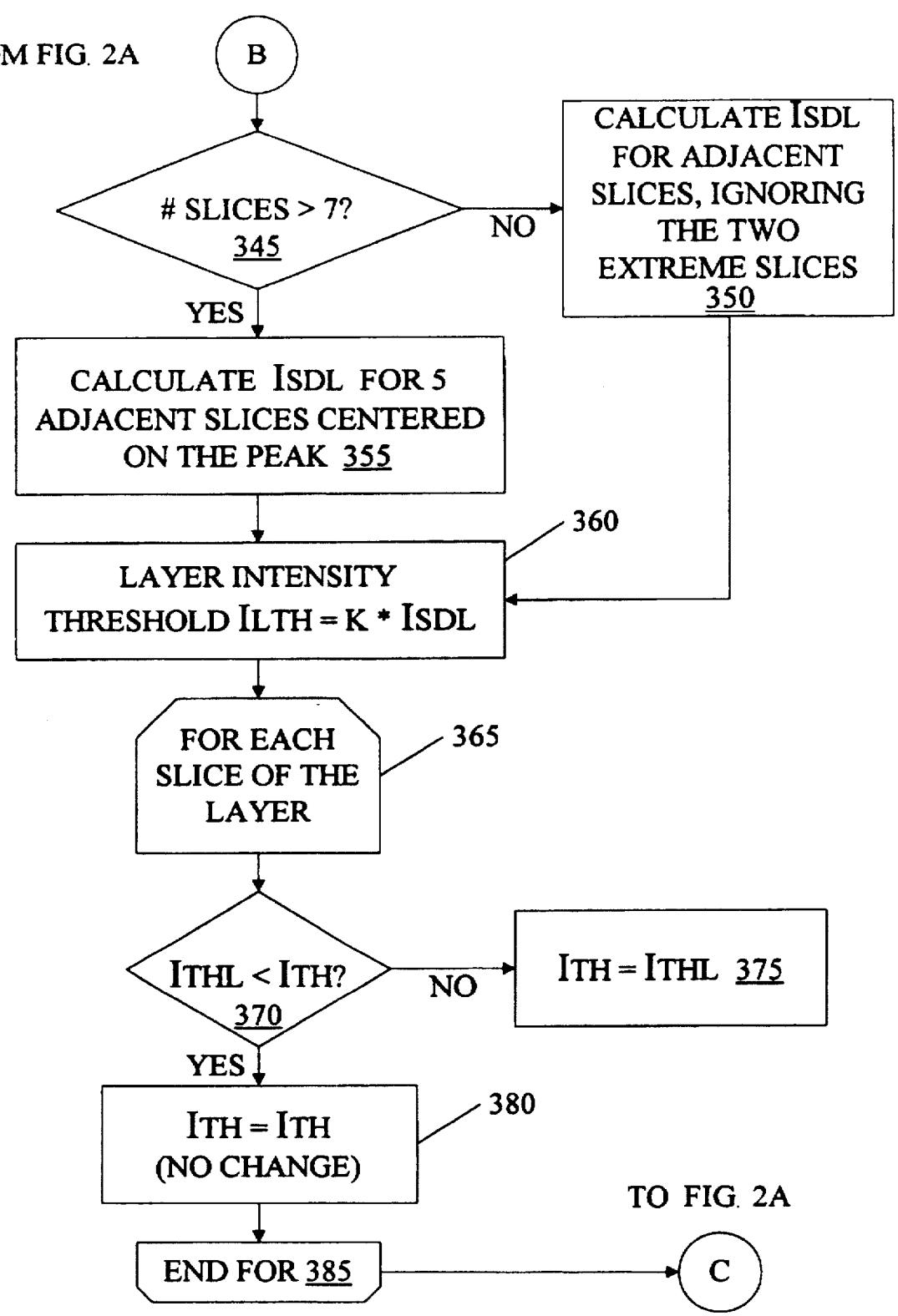

FIGS. 2A and 2B combined are a flowchart depicting the process of establishing multiple error thresholds $I_{TH}$ for a multi-layer reference surface. Beginning with step 300, ADC system 20 screens the pixels of the reference image that correspond with the edges of physical features of the reference image. This screening, or filtering, is used because edge data is typically very noisy in Z.

Edge pixels are typically of much lower intensity than are pixels representing other surface features, with pixels at the center of edges being particularly dark. ADC system 20 uses this attribute to identify edge pixels. In one embodiment, pixels having an intensity value $I_{MAX}$ less than an empirically derived maximum central edge intensity are identified as central edge pixels.

Having identified the central edge pixels, ADC system 20 selects each central edge pixel and determines the edge gradient direction (i.e., the direction perpendicular to the direction of the edge in which the central edge pixel resides) using conventional edge-gradient detection techniques. ADC system 20 examines the intensity values associated with a chain of up to seven sequential pixels extending from the central edge pixel in the direction of the edge gradient. Starting with the pixel closest to the identified central edge pixel and continuing until the intensity value of one of the chain of pixels exceeds an empirically derived maximum edge intensity. Each pixel of the chain is identified as a possible edge pixel. Then, to further discriminate edges, those pixels adjacent to possible edge pixels are identified as near-edge pixels.

Intensity thresholds $I_{TH}$ can vary between the user-defined minimum intensity threshold and the empirically derived maximum threshold. Each identified edge pixel is assigned a default intensity threshold $I_{DTH}$ which is the midpoint between the minimum and maximum intensity-thresholds. The default intensity threshold $I_{DTH}$ is then stored, along with a corresponding default Z level, as one of the intensity thresholds $I_{TH}$ in the intensity-threshold lookup table. The value $Z_{Imax}$ associated with each edge pixel is then assigned the default Z level. An exemplary default Z level is associated with an extreme slice, such as slice zero, that does not include image data.

In step 305 the Z values of the non-edge pixels (those pixels not identified as edge pixels or near-edge pixels) are filtered by replacing each observed z-value with a filtered z-value equal to the average of the observed z-value and the eight observed z values of the adjacent pixels (i.e., the z-value of each pixel is replaced with an average of the z values from a three-by-three matrix of pixels centered on the selected pixel). Of course, other types of filtering may also be used, as will be apparent to those of skill in the art.

Next, in step 310 ADC system 20 calculates the standard deviation of the intensity values for each slice ($I_{SSD}$). Each slice-intensity standard deviation ISSD is then multiplied by a constant K (e.g., K=2.75 in one embodiment) and stored in the intensity-threshold lookup table as an intensity-error threshold $I_{TH}$ (step 315).

In accordance with one embodiment of the invention, pixels of the reference image are grouped according to their respective z values $P_R(Z_{Imax})$ to identify different physical layers of the reference surface. Because different layers of a surface typically have different image properties, such as reflectance and image texture, the groups of pixels are analyzed separately to determine an optimum intensity-error threshold $I_{TH}$ for each of the groups, and therefore for each layer of the reference surface. This aspect of the present invention is illustrated with reference to FIGS. 3A and 3B.

Figure 3A:
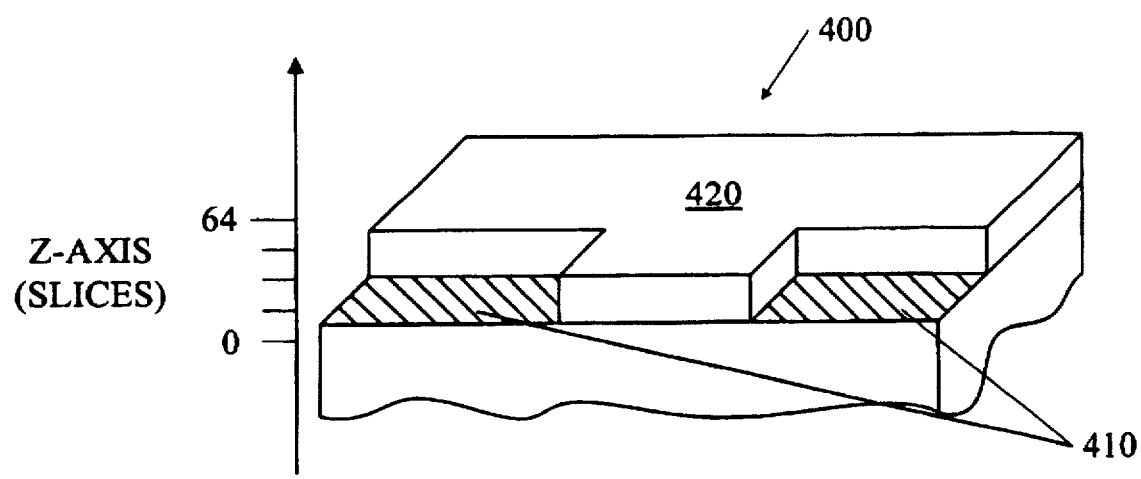
FIG. 3A is a perspective view of a portion of a silicon wafer 400 having a rough surface 410 partially overlaid with a material having a relatively smooth surface 420.
Figure 3B:
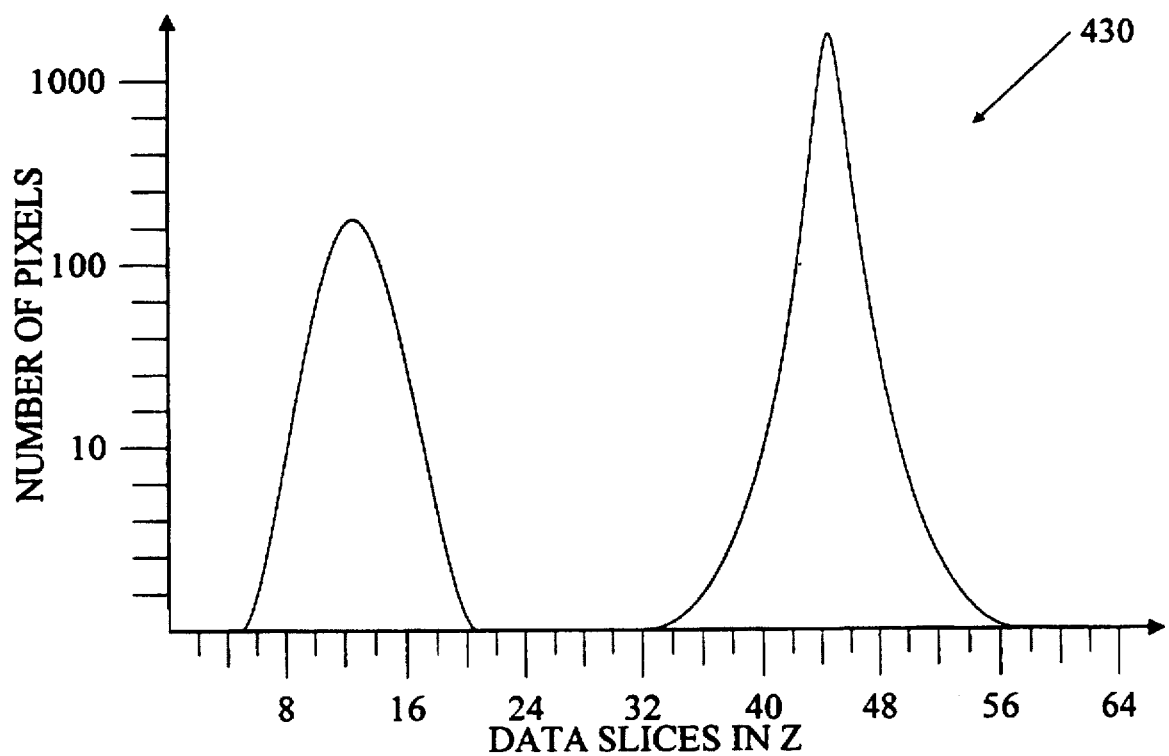
FIG. 3B is a histogram 430 depicting the number of pixels (the number of maximum intensity values $I_{\lambda max}$) for each of 64 "slices" of intensity data.

FIG. 3A is a perspective view of a portion of a silicon wafer 400 having a rough surface 410 partially overlaid with a material having a relatively smooth surface 420. FIG. 3B is a histogram 430 depicting the number of pixels (the number of maximum intensity values $I_{\lambda max}$) for each of 64 "slices" of intensity data. Because the maximum intensity values $I_{max}$ occur when the focal point of confocal optics 50 is coincident with a surface, elevations (slices) associated with a large number of maximum intensity values $I_{max}$ indicate the presence of a surface. In the example of FIGS. 3A and 3B, the two surface layers of wafer 400 are indicated by corresponding peaks of histogram 430.

Histogram 430 is for illustrative purposes. Histograms derived from actual surfaces are typically noisy. Thus, empirically derived histograms are smoothed using conventional techniques. For example, in one embodiment the number of pixels in each slice is replaced with an average of the number of pixels of that slice and the two adjacent slices.

Returning to FIG. 2A, in step 325 ADC system 20 detects the peaks and valleys of the smoothed histogram 430. In one embodiment, a peak is a slice in which the number of pixels is greater than the number of pixels in either adjacent slice, and a valley is a slice in which the number of pixels is fewer than the number of pixels in either adjacent slice. Other schemes may also be used, as will be apparent to those of skill in the art.

Peaks and valleys may be due to noise or to physical features of the reference surface. Some noise is filtered out by requiring the number of pixels in a given slice be greater than a predetermined threshold number before that slice be considered a peak or a valley. In one embodiment ADC system 20 assigns the user-defined minimum intensity threshold to slices having fewer than 50 pixels. Slices having more than 100 pixels are assigned the intensity threshold $I_{SSD}$ derived in step 310. Finally, slices having between 50 and 100 pixels are assigned an intensity threshold linearly interpolated between the minimum intensity threshold and the intensity threshold $I_{SSD}$. For example, a slice having 75 pixels (i.e., midway between 50 and 100) would be assigned an intensity threshold $I_{TH}$ midway between the minimum intensity threshold and the intensity threshold $I_{SSD}$.

Physical layers are further distinguished from noise by requiring a layer be identified by some minimum number consecutive slices between valleys. In the example of FIG. 2A, if the number of slices between valleys is less than three, then the process moves on to the next pair of valleys (decision 335); conversely, if the number of slices between valleys is greater than three, then the process moves on to decision 345 of FIG. 2B.

If a surface layer is between four and seven slices (as indicated by a peak of histogram 430), ADC system 20 calculates the standard deviation of the intensity values $I_{max}$ associated with the pixels of those slices, ignoring the two extreme slices (step 350). For example, if there are five slices between valleys, the standard deviation of the intensity values is calculated for all of the pixels of the middle three slices. If the layer is greater than seven slices, then the standard deviation is calculated for the five adjacent slices centered on the slice between the selected valleys having the highest number of pixels (step 355).

Whether from step 350 or 355, the intensity standard deviation of the pixels in the detected layer is denoted ISDL. The intensity-error threshold $I_{THL}$ for the layer (for each slice identified as representing a physical layer) is calculated by multiplying the constant K (e.g., 2.75) by ISDL (step 360). Next, the layer intensity threshold $I_{THL}$ is compared (step 370) with the intensity-error threshold $I_{TH}$ previously assigned to those slices in step 315. If the layer intensity-error threshold $I_{THL}$ is greater than the previously obtained intensity-error threshold $I_{TH}$, then the intensity-error threshold $I_{TH}$ is updated (i.e., $I_{TH}$ is set equal to $I_{THL}$ in step 375); conversely, if the layer intensity-error threshold $I_{THL}$ is less than or equal to the intensity-error threshold $I_{TH}$ then the intensity-error threshold $I_{TH}$ is retained for subsequent pixel comparisons (step 380). A block 385 represents the end of the loop begun in block 365, after which the process moves to block 340 of FIG. 2A. The process continues thus until each peak of histogram 430 is analyzed and the intensity-error threshold $I_{TH}$ associated with each layer are optimized.

While the present invention has been described in connection with specific embodiments, variations of these embodiments will be obvious to those of ordinary skill in the art. For example, the present invention may be applied to color images. Therefore, the spirit and scope of the appended claims should not be limited to the description of the preferred versions.

What is claimed is:

1. A method comprising:
representing a three-dimensional surface, using a Cartesian coordinate system having x, y, and z axes, as a plurality of points on the surface, wherein each point is represented as a pixel having an intensity value, a unique x-y coordinate, and a z coordinate specified by a z value;

collecting a first group of the pixels having similar z values, the first group representing a first layer of the surface;

collecting a second group of the pixels, each pixel of the second group having a z value similar to the z values of other pixels of the second group and dissimilar to the z values of the pixels of the first group, the second group representing a second layer of the surface;

determining a first error threshold for the intensity values of the first group of pixels; and determining a second error threshold for the intensity values of the second group of pixels.

2. The method of claim 1, further comprising identifying those of the plurality of pixels that represent edges of features on the surface.

3. The method of claim 2, wherein those of the plurality of pixels that represent edges include central edge pixels identified as having intensity values less than a maximum central edge intensity.

4. The method of claim 3, wherein those of the plurality of pixels that represent edges include possible edge pixels identified as having intensity values less than a maximum edge intensity.

5. The method of claim 1, wherein each unique z coordinate has a corresponding number of pixels, and wherein collecting the first group of the pixels comprises:

determining the number of pixels corresponding to each unique z coordinate.

6. The method of claim 5, further comprising collecting groups of z coordinates having similar numbers of pixels.

7. The method of claim 1, wherein each unique z coordinate represents a slice of intensity data, the method further comprising calculating and storing an intensity error threshold for each slice.

8. The method of claim 7, further comprising calculating the intensity standard deviation for each slice.

9. The method of claim 7, wherein collecting the first group of comprises combining at least two adjacent slices of intensity data.

10. The method of claim 9, further comprising calculating the intensity standard deviation for the at least two adjacent slices of intensity data.

11. A system for imaging a three-dimensional surface of an object, the system comprising:

a translation stage configured to support the object;

optics positioned to scan a beam across the surface of the object such that the beam reflects off of the surface from a plurality of surface points;

computation means, connected to the optics, for representing each surface point as a pixel having an intensity value, a unique x-y coordinate, and a z-coordinate specified by a z-value; and threshold optimization means for:

collecting a first group of the pixels having similar z values, the first group representing a first layer of the surface;

collecting a second group of the pixels, each pixel of the second group having a z value similar to the z values of other pixels of the second group and dissimilar to the z values of the pixels of the first group, the second group representing a second layer of the surface;

determining a first error threshold for the intensity values of the first group of pixels; and determining a second error threshold for the intensity values of the second group of pixels.

12. The system of claim 11, further comprising means for identifying those of the plurality of pixels that represent edges of features on the surface.

13. The system of claim 12, wherein those of the plurality of pixels that represent edges include central edge pixels identified as having intensity values less than a maximum central edge intensity.

14. The system of claim 13, wherein those of the plurality of pixels that represent edges include possible edge pixels identified as having intensity values less than a maximum edge intensity.

15. The system of claim 11, wherein each unique z coordinate has a corresponding number of pixels, and wherein the threshold optimization means further comprises means for determining the number of pixels corresponding to each unique z coordinate.

16. The system of claim 15, wherein the threshold optimization means further comprises means for collecting groups of z coordinates having similar numbers of pixels.

17. The system of claim 11, wherein each unique z coordinate represents a slice of intensity data, and wherein the threshold optimization means further comprises means for calculating and storing an intensity error threshold for each slice.

18. The system of claim 17, wherein the threshold optimization means further comprises means for calculating the intensity standard deviation for each slice.

19. The system of claim 17, wherein the means for collecting the first group of pixels comprises means for combining at least two adjacent slices of intensity data.

20. The system of claim 19, wherein the threshold optimization means further comprises means for calculating the intensity standard deviation for the at least two adjacent slices of intensity data.

* * * * *

UNITED STATES PATENT AND TRADEMARK OFFICE
CERTIFICATE OF CORRECTION

PATENT NO. : 5,798,830
DATED : August 25, 1998
INVENTOR(S) : Srinivasan, Lakshman It is certified that error appears in the above-identified patent and that said Letters Patent is hereby corrected as shown below:

Column 1, line 5, replace "a continuation-in-part" with --related to the--;
Column 1, line 5, remove "of";
Column 1, line 10, after "Lee," insert --now abandoned,--;
Column 1, line 16, after "Lee" insert --, now U.S. Patent No. 5,479,252 issued Dec. 26, 1995--;
Column 1, line 24, after "1994" insert --, now U.S. Patent 5,483,055 issued on Jan. 9, 1996--;
Column 1, line 36, after "1994" insert --, now U.S. Patent 5,557113 issued on Sept. 17, 1996--;
Column 1, line 40, after "1995" insert --, now U.S. Patent 5,594,235 issued on Jan. 14, 1997--;
Column 1, line 45, remove "[_____]" and substitute --08/730,238 still pending--
Column 1, line 45, delete ", filed on 30 June 1995";
Column 1, line 48, remove "[_____]" and substitute --08/756,420 still pending--
Column 2, line 45, remove " z " and substitute -- Z --;
Column 4, line 38, remove "in step 215";
Column 4, line 46, remove "300" and substitute "302";
Column 5, line 12, remove "level" and substitute "value";
Column 5, line 14, remove "level" and substitute "value";
Column 5, line 14, remove "level" and substitute "value";
Column 5, line 35, after "surfaces" place --, as in step 320,--;
Column 6, line 16, after "number" place --of--;
Column 6, line 18, after "valleys" place --calculated in step 330--; and
Column 6, line 50, remove "block 340 of" and substitute "C on".

Signed and Sealed this

Ninth Day of January, 2001

Attest:

*Attesting Officer*

Q. TODD DICKINSON
*Commissioner of Patents and Trademarks*